(12) United States Patent
Cho et al.

(10) Patent No.: US 8,830,463 B2
(45) Date of Patent: Sep. 9, 2014

(54) ROTATING-ELEMENT ELLIPSOMETER AND METHOD FOR MEASURING PROPERTIES OF THE SAMPLE USING THE SAME

(75) Inventors: Yong Jai Cho, Yuseong-gu (KR); Won Che Gal, Yuseong-gu (KR); Hyun Mo Cho, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 148 days.

(21) Appl. No.: 13/587,442

(22) Filed: Aug. 16, 2012

(65) Prior Publication Data

US 2013/0044318 A1 Feb. 21, 2013

(30) Foreign Application Priority Data

Aug. 17, 2011 (KR) .................. 10-2011-0081475

(51) Int. Cl.
*G01J 4/00* (2006.01)
*G01N 21/21* (2006.01)

(52) U.S. Cl.
CPC ........ *G01N 21/211* (2013.01); *G01N 2021/213* (2013.01)
USPC ........................................................ 356/369

(58) Field of Classification Search
CPC ... G01N 4/00; G01N 2/211; G01N 2021/211; G01N 2021/213
USPC ........................................................ 356/369
See application file for complete search history.

(56) References Cited

U.S. PATENT DOCUMENTS

| 6,052,188 | A | 4/2000 | Fluckiger et al. | |
|---|---|---|---|---|
| 6,456,376 | B1 * | 9/2002 | Liphardt et al. | 356/369 |
| 6,486,951 | B2 * | 11/2002 | Hirosawa et al. | 356/369 |
| 7,158,231 | B1 * | 1/2007 | Woollam et al. | 356/369 |
| 7,336,361 | B1 * | 2/2008 | Liphardt et al. | 356/369 |
| 7,468,794 | B1 * | 12/2008 | Liphardt et al. | 356/369 |
| 2006/0268272 | A1 * | 11/2006 | Liphardt et al. | 356/369 |
| 2010/0004773 | A1 * | 1/2010 | Kochergin | 700/103 |

FOREIGN PATENT DOCUMENTS

| KR | 10-2001-0053381 A | 6/2001 |
|---|---|---|
| KR | 10-2002-0008697 A | 1/2002 |
| KR | 10-0742982 B1 | 7/2007 |
| KR | 10-2009-0049226 A | 5/2009 |
| KR | 10-2010-0064612 A | 6/2010 |
| KR | 10-2011-0035811 A | 4/2011 |

OTHER PUBLICATIONS

Chen et al., "Multichannel Mueller Matrix Ellipsometer Based on the Dual Rotating Compensator Principle," Thin Solid Films, 2004, pp. 14-23.

* cited by examiner

*Primary Examiner* — Roy M Punnoose
(74) *Attorney, Agent, or Firm* — Sughrue Mion, PLLC

(57) ABSTRACT

Provided is a real-time spectroscopic ellipsometer capable of obtaining information on properties of a sample, a nano pattern shape, in real time by measuring and analyzing, for a plurality of wavelengths, a change in a polarization state of incident light generated while being reflected or transmitted due to the sample when light having a specific polarization component is incident to the sample.

13 Claims, 3 Drawing Sheets

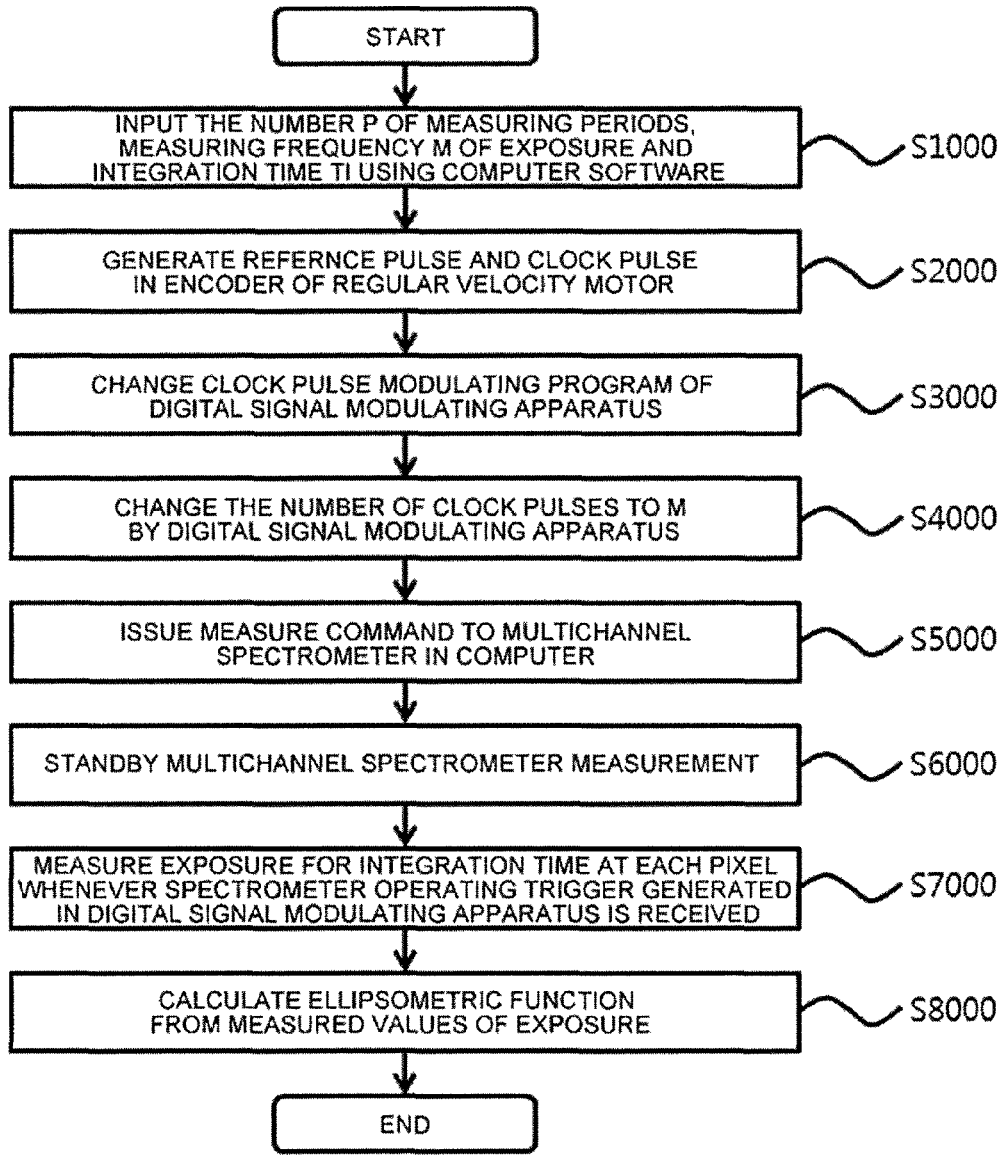

ROTATING-ELEMENT ELLIPSOMETER AND METHOD FOR MEASURING PROPERTIES OF THE SAMPLE USING THE SAME

CROSS-REFERENCE TO RELATED APPLICATIONS

This application claims priority under 35 U.S.C. §119 to Korean Patent Application No. 10-2011-0081475, filed on Aug. 17, 2011, in the Korean Intellectual Property Office, the disclosure of which is incorporated herein by reference in its entirety.

TECHNICAL FIELD

The following disclosure relates to a rotating-element multichannel ellipsometer, and more particularly, to a real-time ellipsometer used to measure properties of a sample by measuring and analyzing a change in a polarization state of light reflected or transmitted by the sample in real time.

BACKGROUND

Importance of a technology capable of measuring and evaluating properties such as optical properties, a shape of nano patterns, and the like, of nano samples in real time by a non-destructive manner or a non-contact manner during a manufacturing process, in industrial fields related to a semiconductor device, a flat panel display, nanobio, nanoimprint, thin film optics, and the like, which have been rapidly developed has been gradually increased. Therefore, in an ellipsometry used as measuring equipment for process in the industrial fields, the measuring precision and measuring accuracy have been gradually improved and the continuous improvement of a measuring speed for real-time measurement has been required.

A multichannel spectroscopic ellipsometer as shown in FIG. 1 among multichannel spectroscopic ellipsometers of the related art has been the most widely used. The multichannel spectroscopic ellipsometer has been well known as nano measuring equipment that uses a basic principle of measuring and analyzing a change in a polarization state of reflected light 300 or transmitted light by the sample 200 for a plurality of wavelengths when incident light 100 is incident to the sample 200 to find properties of the sample.

Describing core components of the multichannel spectroscopic ellipsometers of the related art, a light source 110, an achromatic aberration collimator 120 that changes light emitted from the light source 110 into parallel light, and a polarization modulation unit 125 that forms the parallel light into a specific polarization state are disposed on a line of the incident light 100 and a polarization analysis unit 305 that is an optical system for analyzing the polarization state of the reflected light, and an achromatic aberration optical focus system 330 that intensively irradiates the parallel light transmitting the polarizing analysis unit 305 on a local area is disposed on a line of the reflected light 300, wherein the intensively irradiated light transmits an optical fiber 340 or is directly incident to a slit of a multichannel spectrometer 350. The multichannel spectrometer includes a dispersion optical system 352 and a multichannel photometric detector 354 and the light transmitting the slit is dispersed by the dispersion optical system 352 to be irradiated on each pixel of the multichannel photometric detector 354 for each wavelength and a quantity of light incident to each pixel is measured as an electrical signal such as voltage or current.

Among various types of multichannel spectroscopic ellipsometers of the related art, a rotating-polarizer or analyzer spectroscopic ellipsometer and a rotating-compensator spectroscopic ellipsometer have been the most widely used, each of which uses a least-squares algorithm analysis method that measures Fourier coefficients or ellipsometric functions about a waveform of the intensity of light measured by the photometric detector when a linear polarizer or a compensator rotates at a predetermined speed by a multichannel photometric detector in real time and uses the measured values and a theoretical model for a sample to find properties of a sample.

A core component of the rotating-polarizer multichannel spectroscopic ellipsometers of the related art is configured of a linear polarizer in which the polarization modulation unit 125 rotates at constant velocity of FIG. 1, which is generally referred to as the polarizer. The polarization analysis unit 305 is configured of a linear polarizer that stops at any azimuth, which is generally referred to as an analyzer. Meanwhile, core components of the rotating-analyzer multichannel spectroscopic ellipsometer are the same as the components of the rotating-polarizer multichannel spectroscopic ellipsometer except that the polarizer, that is, the polarization modulation unit 125 is in a stop state and the analyzer instead rotates at constant velocity. Therefore, the rotating-polarizer (or analyzer) multichannel spectroscopic ellipsometers of the related art have the most ideal advantage in terms of spectroscopic measurement since the number of configured optical elements is relatively smallest and only the optical elements of achromatic aberration such as a prism linear polarizer are used. However, the rotating-polarizer multichannel spectroscopic ellipsometers of the related art have a critical disadvantage called residual polarization of the light source and the rotating-analyzer multichannel spectroscopic ellipsometers need to solve the polarization dependency problem of the photometric detector by calibration.

Meanwhile, the rotating-compensator multi-channel spectroscopic ellipsometers of the related art may be classified into a single rotating compensator and a double rotating compensator. First, the core structure of the single rotating-compensator multichannel spectroscopic ellipsometers is the same as the core structure of the rotating-polarizer multichannel spectroscopic ellipsometers of the related art except that the polarizer stops and the compensator rotating at constant velocity is added between the polarizer and the sample or between the sample and the analyzer.

Meanwhile, the core structure of the double rotating-compensator multichannel spectroscopic ellipsometers of the related art has the same structure of the single rotating-compensator multichannel spectroscopic ellipsometers of the related art except that one compensator is further added so that the compensators are each disposed at both sides of the sample, wherein these compensators each rotate at a uniform velocity ratio of an integer. Therefore, in the core structure of the rotating-compensator multichannel spectroscopic ellipsometers of the related art, the polarizer and the analyzer are in a stop state at the time of measurement. Therefore, the rotating-compensator multichannel spectroscopic ellipsometers of the related art does not have a problem of the polarization dependency problem of the light source and the photometric detector. However, for a broadband wavelength λ region, it is very difficult to manufacture the achromatic aberration compensator having a phase difference of λ/4. As a result, there are problems in terms of dispersion characteristics and equipment calibration of the compensator, complexity of a method for analyzing data, and the like.

Meanwhile, in order to obtain the Fourier coefficients or the ellipsometric functions for the waveform of the intensity of light, the rotating-element multichannel ellipsometers of the related art uses a fixed exposure measuring frequency per unit rotation and a fixed integration time of the multichannel photometric detector that is equal to an exposure measuring period. In order to measure the Fourier coefficients or the ellipsometric functions, the rotating-element multichannel ellipsometers of the related art adopts a method for measuring the exposure of a predetermined frequency M per unit measurement by each pixel of the multichannel photometric detector at a plurality of azimuths at equidistance for one turn period or a half of the turn period of the optical element while at least one optical element rotating at constant velocity. The rotating-polarizer or analyzer multichannel spectroscopic ellipsometers of the related art mainly use the case in which the exposure measuring frequency M per unit measurement is fixed to 4, the single rotating-compensator multichannel spectroscopic ellipsometers of the related art mainly use the case in which M is fixed to 8, and the double rotating-compensator multichannel spectroscopic ellipsometers of the related art mainly use the case in which M is fixed to 36.

Meanwhile, in the case of the rotating-element ellipsometers of the related art, since the difference in the intensity of light reflected or transmitted by the sample according to the material and structure of the sample is generally large, the integration time needs to increase so as to reduce the measuring error when the intensity of light to be measured is weak, but may be limited by the predetermined exposure measuring period.

To the contrary, when the measured intensity of light is excessively large, the photometric detector reaches a saturation state and therefore, the integration time needs to be reduced. In this case, as the integration time is smaller than the exposure measuring period, the standby time of the photometric detector is longer and longer, such that the measuring precision may be deteriorated.

When the intensity of light periodically changing over time t is measured in real time by using the integrating photometric detector, the rotating-element ellipsometer uses a method for analyzing a Fourier coefficient so as to analyze the waveform. Provided that there is no error in the measuring apparatus, the light intensity I(t) measured by the integrating photometric detector using electrical signal such as voltage or current for a specific wavelength may be represented by the following Equation.

$$I(t) = I_{dc}\left\{1 + \sum_{n=1}^{N} [\alpha_{2n}\cos(4\pi nt/T) + \beta_{2n}\sin(4\pi nt/T)]\right\} \quad (1)$$

In the above equation, $I_{dc}$ represents an average value of the intensity of light (or referred to as a 0-order Fourier coefficient), $\alpha_{2n}$ and $\beta_{2n}$ represent normalized Fourier coefficients, and T represents a period. Here, 2N is not 0 but is a natural number that represents a highest order among the normalized Fourier coefficients.

Among various types of the rotating-element multichannel ellipsometers of the related art, in the case of the rotating-polarizer or rotating-analyzer multichannel ellipsometers of the related art, all the Fourier coefficients other than the normalized Fourier coefficients of a secondary term such as α2 and β2 in Equation (1) that is the intensity of light measured by the multichannel photometric detector have a value of 0 and therefore, N becomes 1.

In the case of the single rotating-compensator multichannel ellipsometers of the related art, only the Fourier coefficients of second and fourth-order terms such as $\alpha_2$, $\beta_2$, $\alpha_4$, and $\beta_4$ are not 0 and therefore, N becomes 2. Meanwhile, in the case of the double rotating-compensator ellipsometers of the related art, the Fourier coefficients of the effective highest order term in Equation (1) are $\alpha_{32}$ and $\beta_{32}$ when two compensators rotate at constant velocity at a predetermined velocity ratio of 5:3 and therefore, N becomes 16.

In the multichannel ellipsometers, a method of more accurately obtaining the normalized Fourier coefficients $\alpha_{2n}$ and $\beta_{2n}$ from the waveform of the intensity of light measured by the photometric detector as in the above Equation 1 is very important. The rotating-element multichannel ellipsometers of the related art that are the most widely spread have mainly used a CCD detector array, a photodiode detector array, and the like, as the multichannel photometric detector. The multichannel photometric detectors are referred to as the integrating photometric detector since the measured light quantity value is proportional to the intensity of light as well as integration time. The integrating photometric detector reduces or increases the integration time when the quantity of light is too large or insufficient at the time of measurement to perform the measurement under the appropriate conditions. However, the integration time needs to be equal or larger to or than the minimum integration time of the corresponding photometric detector at the time of measurement.

In order for the rotating-element multichannel ellipsometers of the related art to obtain the Fourier coefficients, the intensity of light periodically changing over time as in the equation (1) is measured by being divided M times per unit measurement at a predetermined time interval by the multichannel integrating photometric detector. In this case, the integration time accurately coincides with the divided time interval. For example, the exposure $S_j$ measured under the conditions of, for example, $T_i = T/M$ is represented by the following Equation (2).

$$S_j = \int_{(j-1)T/M}^{jT/M} I(t)dt, (j = 1, 2, 3, \ldots, M) \quad (2)$$

$$= \frac{I_{dc}T}{M} + \sum_{n=1}^{N} \frac{I_{dc}T}{2n\pi} \sin\left(\frac{2n\pi}{M}\right)$$

$$\left\{\alpha_{2n}\cos\left[\frac{2n\pi(2j-1)}{M}\right] + \beta_{2n}\sin\left[\frac{2n\pi(2j-1)}{M}\right]\right\}$$

When solving the normalized Fourier coefficient by a simultaneous equation like the above Equation (2), the Equation of the normalized Fourier coefficients $\alpha_{2n}$ and $\beta_{2n}$ represented by the exposure $S_j$ is obtained, which is referred to as Hadamard transform and has been used as a representative method of obtaining Fourier coefficients in the rotating-element multichannel ellipsometers of the related art. Therefore, only the multichannel integrating photometric detectors specially designed and manufactured to satisfy the conditions is used. However, the actual integrating photometric detectors read out the quantity of light accumulated in each pixel for the integration time and do not react with the incident light for the time initializing the state, that is, the readout time $T_r$. Therefore, the exposure of the above Equation (2) is corrected to the following Equation (3) in consideration of this situation.

$$S_j = \int_{(j-1)T/M+T_r}^{T/M} I(t)dt, (j=1,2,3,\ldots,M) \quad (3)$$

In this case, under the assumption that the readout time $T_r$ is very shorter than the measuring time interval T/M of exposure, an equation obtained by performing first-order approximation on $T_r$ is used.

In the case of the rotating-polarizer or analyzer multichannel ellipsometers of the related art using the Hadmard transform, in the above Equation (1), T represents a mechanical turn period of the polarizer or the analyzer, N is 1 as described above, and the minimum value of the measuring frequency M of exposure measured for period T/2 is 3. However, $\beta_4$ is additionally measured in order to see whether the system is in a normal state and thus, the measuring frequency of exposure is increased to 4. In this case, since the exposure values measured in each period have symmetry with respect to a period of T/2, four unknown coefficients $I_{dc}$, $\alpha_2$, $\beta_2$, and $\beta_4$ can be measured from a simultaneous equation configured of only $S_1$, $S_2$, $S_3$, and $S_4$ measured at a first half period.

Meanwhile, in the case of the single rotating-compensator multichannel ellipsometers of the related art using the Hadamard transform, T represents the mechanical turn period of the compensator, N is 2, and the minimum value of the frequency M of exposure measured for period T/2 is 5. However, $\beta_8$ is additionally measured so as to see whether the system is in a normal state and thus, the measuring frequency of exposure is increased to 8. In order to obtain six unknown coefficients $I_{dc}$, $\alpha_2$, $\beta_2$, $\alpha_4$, $\beta_4$, and $\beta_8$ from the measured value of $S_j$ (j=1, 2, 3, . . . , 8) in consideration of the symmetry of the value of exposure measured like the previous case, the solution of simultaneous equation is used. In addition, in the case of the double rotating-compensator multichannel ellipsometers of the related art using the Hadamard transform, thirty six unknown coefficients are each obtained in a very complex form by solving thirty six simultaneous equations.

In the rotating-element multichannel ellipsometers of the related art, when the turn period of the optical element is T, the measured period is limited to T/2 or T and equations of different complex forms obtained by solving the simultaneous equation of Equation (2) for the measuring frequency M of exposure per unit measurement one by one are used. In addition, a method for correcting the readout time error by using the first-order approximation equation for the readout time for Equation (3) for the measured values $S_j$ of exposure to obtain the average value $I_{dc}$ of the intensity of light and the normalized Fourier coefficients $\alpha_{2n}$ and $\beta_{2n}$ is used. Therefore, the integration time of the photometric detector used in the rotating-element multichannel ellipsometers of the related art is fixed to T/M or has only a value smaller than T/M and as a result, it is impossible to increase the integration time by reducing the measuring frequency of exposure or changing the measuring period.

When using the Hadamard transform of the related art, a sum of the readout time and the integration time needs to be set to accurately coincide with the measuring time interval. Therefore, when the intensity of light is too strong, the quantity of light easily reaches the saturation state even for the short integration time and thus, a part of light beam needs to be blocked by additionally using the optical elements such as an iris diaphragm, a neutral density filter (ND filter), and the like, inevitably so as to reduce the output from the light source. To the contrary, when the intensity of light is weak, there is a need to increase the integration time, but an apparatus for the measuring period and the measuring frequency of exposure specially set according to a kind of the multichannel ellipsometers of the related art is configured and used and thus, the maximum value of the integration time may be limited to T/M.

A need exists for a development of new multichannel ellipsometers capable of solving the above problems.

RELATED ART DOCUMENT

Patent Document (Patent Document 1) KR 742982 B Jul. 20, 2007
(Patent Document 2) KR 2009-49226 A May 18, 2009
(Patent Document 3) KR 2011-35811 Apr. 6, 2011

SUMMARY

An exemplary embodiment of the present invention is directed to providing a rotating-element ellipsometer capable of more easily and precisely measuring Fourier coefficients for a waveform of the intensity of light by solving problems of complexity of equipment or degradation of measuring precision due to addition of an optical system caused by limiting integration time of a photometric detector of a rotating-element ellipsometer of the related art.

Another exemplary embodiment of the present invention is directed to providing a rotating-element ellipsometer capable of accurately measuring properties of a sample by more precisely acquiring Fourier coefficients for a waveform of the intensity of light by simple calculation.

Another exemplary embodiment of the present invention is directed to providing a rotating-element ellipsometer with improved measuring precision by rapidly and easily changing integration time and a measuring frequency of exposure with computer software.

Another exemplary embodiment of the present invention is directed to providing a multichannel spectroscopic ellipsometer capable of accurately measuring properties of a sample in real time by solving a residual polarization problem of a light source or a polarization dependency problem of a photometric detector, a wavelength dependency problem of a compensator, problems such as a limitation of a change in integration time due to a fixing of a measuring period and a measuring frequency of exposure, and the like, in a rotating-element multichannel spectroscopic ellipsometers of the related art.

Another exemplary embodiment of the present invention is directed to providing a multichannel spectroscopic ellipsometer configured of three polarizers with the improved structure and function so as to more accurately and rapidly measure properties of a sample than the related art.

Another exemplary embodiment of the present invention is directed to providing a rotating-polarizer multichannel spectroscopic ellipsometer capable of solving a residual polarization problem of a light source.

Another exemplary embodiment of the present invention is directed to providing a rotating-analyzer multichannel spectroscopic ellipsometer with improved measuring accuracy by solving a polarization dependency problem of a photometric detector.

An exemplary embodiment of the present invention provides an ellipsometer including a light source, a polarization modulating unit, a sample stage, a polarization analysis unit, and a photometric detector, the ellipsometer including a digital signal modulating apparatus connected to an optical element unit rotating at constant velocity of the polarization modulating unit or the polarization analysis unit to control a measuring frequency of exposure of the photometric detector. The digital signal modulating apparatus may be connected to the photometric detector and may receive a pulse signal from the optical element unit and transmit a signal controlling the measuring frequency of exposure of the photometric detector according to the measuring conditions and the photometric detector may measure the exposure corresponding to the measuring frequency accordingly. The measuring conditions may be the intensity of light and the digital signal modulating apparatus may control integration time and the measuring frequency of exposure of the photometric detector according to the intensity of light.

The integration time and the measuring frequency of exposure may be controlled by computer program.

The intensity of light may be changed at a predetermined period over time and the ellipsometer according to the exemplary embodiment of the present invention includes an operator, wherein the operator acquires a plurality of values of exposure for a waveform of the intensity of light at a predetermined interval for any multiple of the period from the photometric detector and performs discrete Fourier transform on the plurality of values of exposure to determine a plurality of Fourier coefficients and average value component for the waveform of the intensity of light.

An Equation about the value of exposure $S_j$ may be $S_j = \int_{(j-1)pT/M+T_d}^{(j-1)pT/M+T_d+T_i} I(t)dt$, ($j=1, 2, 3, \ldots, M$) and non-normalized Fourier coefficients $A_{2n}$ and $B_{2n}$ of waveform of intensity of light and average value $I_{dc}$ of intensity of light may each be $$A_{2n} = \frac{\xi_{2n}}{T_i \sin(\xi_{2n})} \left\{ a_{2n} \cos\left[\xi_{2n}\left(1 + \frac{2T_d}{T_i}\right)\right] - b_{2n} \sin\left[\xi_{2n}\left(1 + \frac{2T_d}{T_i}\right)\right] \right\}$$

$$B_{2n} = \frac{\xi_{2n}}{T_i \sin(\xi_{2n})} \left\{ a_{2n} \sin\left[\xi_{2n}\left(1 + \frac{2T_d}{T_i}\right)\right] + b_{2n} \cos\left[\xi_{2n}\left(1 + \frac{2T_d}{T_i}\right)\right] \right\}$$

$$I_{dc} = d_0 / T_i$$

where, {T: Dynamic turn period of optical element rotating at constant velocity

P: The number of measuring periods (positive multiple of ½)

M: Measuring frequency of exposure at predetermined time interval for measuring period pT $T_d$: Delay time $T_i$: Integration time $$I(t) = I_{dc} + \sum_{n=1}^{N} [A_{2n}\cos(4\pi nt/T) + B_{2n}\sin(4\pi nt/T)]$$

$I(t)$: Intensity of light $I_{dc}$: Average value of intensity of light or 0-order Fourier coefficient $A_{2n}, B_{2n}$: Fourier coefficients 2N: Natural number representing highest order among Fourier coefficients except for 0

$$\xi_n = \frac{n\pi T_i}{T}$$

$$a_{2n} = \frac{2}{M} \sum_{j=1}^{M} S_j \cos\left(\frac{4n\pi(j-1)p}{M}\right)$$

$$b_{2n} = \frac{2}{M} \sum_{j=1}^{M} S_j \sin\left(\frac{4n\pi(j-1)p}{M}\right)$$

-continued $$d_0 \equiv \frac{1}{M} \sum_{j=1}^{M} S_j$$

The properties for the sample such as interfacial characteristic, a thin film thickness, a complex refractive index, a nano shape, anisotropic characteristic, surface roughness, a composition ratio, crystallinity, and the like, may be analyzed from the Fourier coefficients $I_{dc}/I_{00}$, $A_{2n}/I_{00}$, $B_{2n}/I_{00}$; $n=1, 2, 3, \ldots$) or ($I_{dc}/I_{00}$, $A_{2n}/I_{dc}$, $B_{2n}/I_{dc}$; $n=1, 2, 3, \ldots$), in which the common component $I_{00}$ is defined as $I_{00}=R_u T_s$, $R_u$ the non-polarization reflectance of the sample, and $T_s$ a term related to the transmittance in the straight-through optical configuration of the ellipsometer.

According to the exemplary embodiment of the present invention, ellipsometric functions may be obtained by limitedly selecting a part of the Fourier coefficients $I_{dc}$, $A_{2n}$, $B_{2n}$; $n=1, 2, 3, \ldots,$ ).

The ellipsometer may be any one of a rotating-polarizer ellipsometer, a rotating-analyzer ellipsometer, a single rotating-compensator ellipsometer, a double rotating-compensator ellipsometer, and other various rotating-element ellipsometers.

According to the exemplary embodiment of the present invention, a method for determining Fourier coefficients uses the ellipsometer. In this case, the intensity of light may be changed at a predetermined period over time and a plurality of values of exposure for a waveform of the intensity of light at a predetermined interval for any multiple of the period may be acquired from the photometric detector and a plurality of Fourier coefficients and average value component for the waveform of the intensity of light may be determined by performing discrete Fourier transform on the plurality of values of exposure. In this case, the Equation about the value of exposure $S_j$ and the Equation of the non-normalized Fourier coefficients $A_{2n}$ and $B_{2n}$ of the waveform of the intensity of light and the average value $I_{dc}$ of the intensity of light may be used.

Another exemplary embodiment of the present invention provides an ellipsometer including: a light source emitting white light to a sample disposed on a sample stage; an achromatic aberration collimator disposed between the light source and the sample stage on a progress path of light and forming the white light emitted from the light source into parallel light; a first polarizer disposed between the achromatic aberration collimator and the sample stage on the progress path of light and receiving the parallel light and polarizing the parallel light; a second polarizer disposed between the first polarizer and the sample stage on the progress path of light and receiving light transmitting the first polarizer and rotating at constant velocity for polarizing the incident light; a sample stage supporting the sample; a third polarizer receiving light with the changed polarization state while being reflected or transmitted by the sample after being polarized by transmitting the second polarizer polarizing the incident light; an achromatic aberration optical focus system receiving the light transmitting the third polarizer and intensively irradiating the incident light to a local region of a multichannel spectrometer; and a multichannel spectrometer receiving the light transferred by the achromatic aberration optical focus system, separating the incident light for each wavelength using the dispersion optical system, irradiating the light separated for each wavelength to the multichannel photometric detector, and measuring the exposure of light irradiated to the multichannel photometric detector for each pixel of the multichannel photometric detector, whereby properties of the sample are measured.

Another exemplary embodiment of the present invention provides an ellipsometer including: a light source emitting white light to a sample stage; an achromatic aberration collimator disposed between the light source and the sample stage on a progress path of light and forming the white light emitted from the light source into parallel light; a first polarizer disposed between the achromatic aberration collimator and the sample stage on the progress path of light and receiving the parallel light and polarizing the parallel light; a sample stage supporting the sample; a second polarizer receiving the light polarized by transmitting the first polarizer and having the changed polarization state while being reflected or transmitted by the sample and rotating at constant velocity for polarizing the incident light; a third polarizer receiving light transmitting the second polarizer and polarizing the incident light; an achromatic aberration optical focus system receiving the light transmitting the third polarizer and intensively irradiating the incident light to a local region of a multichannel spectrometer; and a multichannel spectrometer receiving the light transferred by the achromatic aberration optical focus system, separating the incident light for each wavelength using the dispersion optical system, irradiating the light separated for each wavelength to the multichannel photometric detector, and measuring the exposure of light irradiated to the multichannel photometric detector for each pixel of the multichannel photometric detector, whereby properties of the sample are measured.

The ellipsometer may include the digital signal modulating apparatus for controlling the number of measuring periods and the measuring frequency of exposure by the computer program and the digital signal modulating apparatus may control the integration time of the photometric detector according to the intensity of light irradiated to the multichannel photometric detector.

The ellipsometer may perform the discrete Fourier transform on the exposure measured for the integration time arbitrarily set by the multichannel photometric detector at a predetermined time interval for time (pT: p=½, 1, 3/2, 2, . . . ) of a multiple of ½ of the optical element turn period T to calculate the plurality of Fourier coefficients $I_{dc}$, $A_2$, $B_2$, $A_4$, and $B_4$. The ellipsometer may include an operator performing the calculation.

$\psi$, $\Delta$, and $R_u$ or N, C, and $R_u$ may be calculated from at least three of the plurality of Fourier coefficients.

The properties for the sample such as interfacial characteristic, a thin film thickness, a complex refractive index, a nano shape, anisotropic characteristic, surface roughness, a composition ratio, crystallinity, and the like, may be analyzed from the measured Fourier coefficients $I_{dc}/I_{00}$, $A_2/I_{00}$, $B_2/I_{00}$, $A_4/I_{00}$, and $B_4/I_{00}$ or $I_{dc}/I_{00}$, $A_2/I_{dc}$, $B_2/I_{dc}$, $A_4/I_{dc}$, and $B_4/I_{dc}$ or the measured ellipsometric functions $\psi$, $\Delta$, and $R_u$ or N, C, and $R_u$.

The measuring data of the measured Fourier coefficients $I_{dc}$, $A_2$, $B_2$, $A_4$, and $B_4$ or the measured ellipsometric functions $\psi$, $\Delta$, and $R_u$ or N, C, and $R_u$ may be obtained, the optical theoretical Equation for the sample may be established, the data of the Fourier coefficients or the ellipsometric functions calculated using the plurality of unknown parameters for the region set for the established theoretical Equation may be obtained, the continuous function for the unknown parameters may be obtained from the data obtained from the calculation, and the properties of the sample may be obtained by optimizing the continuous function by applying the least-squares algorithm to the measuring data.

The multichannel photometric detector is configured of a CCD, a CMOS, or a photodiode, wherein the plurality of pixels may be arranged in a linear or two-dimensional plane structure.

The ellipsometer may include a remote light source blocking apparatus disposed after the light source on the progress path of light and blocking the light irradiated to the sample from the light source by a remote control.

The ellipsometer according to the exemplary embodiment of the present invention may include: a first hollow shaft stepping motor attached to the first polarizer to control an azimuth of the first polarizer; a second hollow shaft stepping motor attached to the third polarizer to control an azimuth of the third polarizer; a hollow shaft constant velocity rotating motor attached to the second polarizer to rotate the second polarizer at constant velocity; and an optical encoder attached to the hollow shaft constant velocity rotating motor to rotate together with the hollow shaft constant velocity rotating motor and generating one reference pulse and a plurality of clock pulses for each rotation.

The clock pulses generated from the encoder may be transferred to the digital signal modulating apparatus and the digital signal modulating apparatus may generate the specific number of spectrometer operating triggers at equidistance by the pulses. The generated spectrometer operating triggers may be transferred to the multichannel spectrometer to measure the exposure for the integration time set at each pixel whenever the multichannel photometric detector receives the spectrometer operating trigger.

The digital signal modulating apparatus may change the measuring period or the measuring frequency of exposure according to the intensity of light irradiated to the multichannel photometric detector to control the integration time of the photometric detector.

The ellipsometric functions may be obtained by limitedly selecting the Fourier coefficients with relatively excellent signal to noise ratio among the Fourier coefficients $I_{dc}$, $A_2$, $B_2$, $A_4$, and $B_4$.

The ellipsometer according to the exemplary embodiment of the present invention may include the optical fiber disposed between the achromatic aberration optical focus system and the multichannel spectrometer. The optical fiber may be a single optical fiber. A light receiving unit side may be a bundle of a single optical fiber and a side connected to the multichannel spectrometer may be a bundle of a branched optical fiber formed of a bundle of at least two optical fibers.

Another exemplary embodiment of the present invention provides a method for measuring properties of a sample using a multichannel spectroscopic ellipsometer according to an exemplary embodiment of the present invention including: inputting the number p of measuring period, a measuring frequency M of exposure, and integration time $T_i$ by computer program; generating a reference pulse and a clock pulse by an encoder of a regular velocity rotating motor; changing, by a digital signal modulating apparatus, clock pulse modulating program; issuing, by the computer program, a measuring command to a multichannel spectrometer; waiting the multichannel spectrometer to prepare measurement; measuring the exposure of light reflected or transmitted from the sample for integration time at each pixel of the multichannel photometric detector by receiving a spectrometer operating trigger generated by the digital signal modulating apparatus; and calculating ellipsometric functions from the measured values of exposure, whereby properties of the sample are measured.

Other features and aspects will be apparent from the following detailed description, the drawings, and the claims.

BRIEF DESCRIPTION OF THE DRAWINGS

FIG. 5 is a flow chart for describing a method for changing a measuring frequency of exposure using computer software according to an exemplary embodiment of the present invention.

[Detailed Description of Main Elements]

Figure 1:
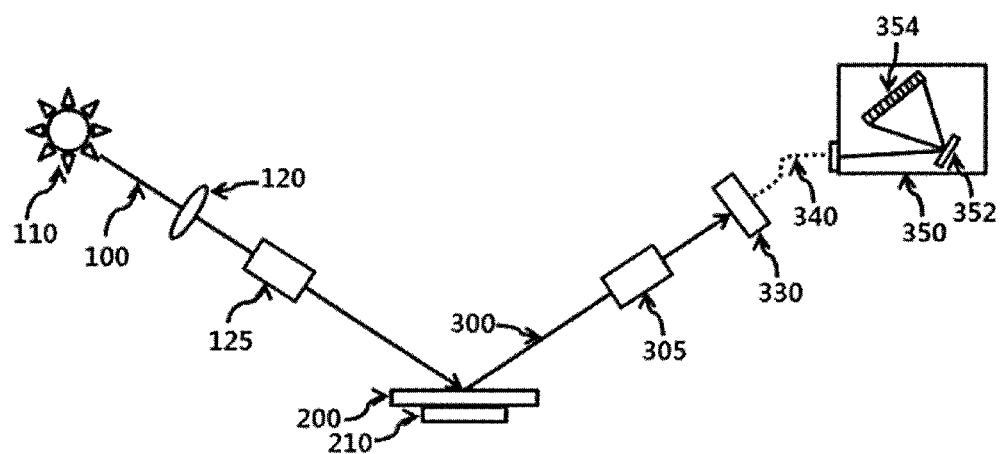
FIG. 1 is a schematic diagram of a multichannel spectroscopic ellipsometer according to the related art.

| | | | |
|---|---|---|---|
| 100: | Incident light | 110: | Light source |
| 120: | Achromatic aberration collimator | | |
| 125: | Polarization modulation unit | 130: | First polarizer |
| 140: | First hollow shaft stepping motor | | |
| 150: | Second polarizer | | |
| 160: | Hollow shaft constant velocity rotating motor | | |
| 200: | Sample | 210: | Sample stage |
| 300: | Reflected light | | |
| 305: | Polarization analysis unit | | |
| 310: | Second hollow shaft stepping motor | | |
| 320: | Third polarizer | | |
| 330: | Achromatic aberration optical focus system | | |
| 340: | Optical fiber | | |
| 350: | Multichannel spectrometer | | |
| 352: | Dispersion optical system | | |
| 354: | Multichannel photometric detector | | |
| 410: | Remote light source blocking apparatus | | |
| 420: | Data transmission line | | |
| 430: | Digital signal modulating apparatus | | |
| 440: | Data transmission line | | |
| 450: | Achromatic aberration optical focus system | | |
| 460: | Achromatic aberration collimator | | |
| 500: | Incident surface | | |
| 510: | Incident reference axis | | |
| 520: | First polarizer transmitting axis direction | | |
| 530: | Second polarizer transmitting axis direction | | |
| 540: | Third polarizer transmitting axis direction | | |

DETAILED DESCRIPTION OF EMBODIMENTS

Hereinafter, exemplary embodiments will be described in detail with reference to the accompanying drawings so that the present invention can be easily practiced by those skilled in the art to which the present invention pertains. However, in describing embodiments of the present invention, detailed descriptions of well-known functions or constructions will be omitted so as not to obscure the description of the present invention with unnecessary detail.

In addition, like or similar reference numerals denote parts performing similar functions and actions throughout the drawings. In addition, unless explicitly described otherwise, "comprising" any components will be understood to imply the inclusion of other components but not the exclusion of any other components.

A configuration and a function of a rotating-element multichannel spectroscopic ellipsometer according to an exemplary embodiment of the present invention will be described below. First, FIGS. 2 and 3 are diagrams schematically showing a configuration of a multichannel spectroscopic ellipsometer according to an exemplary embodiment of the present invention for achieving the above objects.

Figure 2:
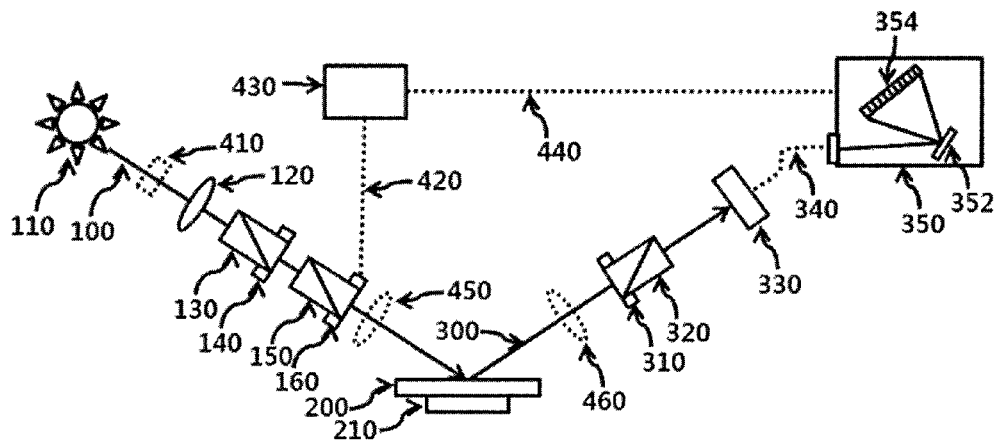
FIG. 2 is a schematic diagram of a multichannel spectroscopic ellipsometer according to a first exemplary embodiment of the present invention.
Figure 3:
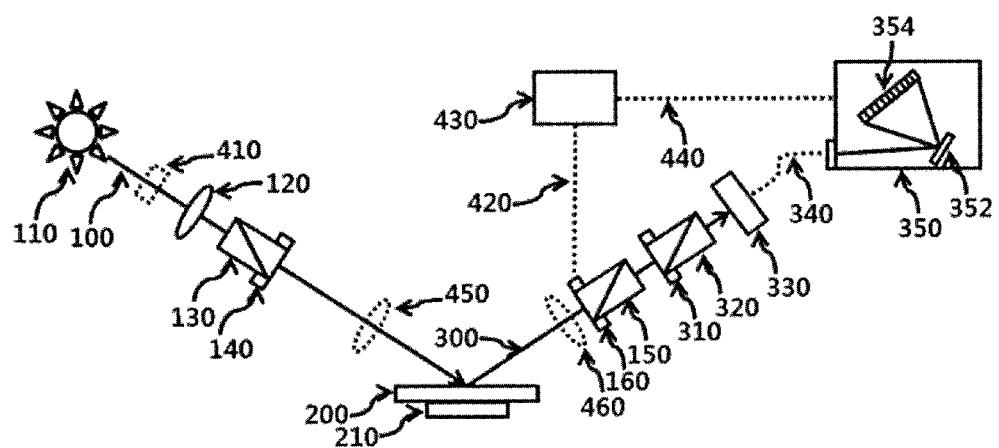
FIG. 3 is a schematic diagram of a multichannel spectroscopic ellipsometer according to a second exemplary embodiment of the present invention.

As shown in FIG. 2, the multichannel spectroscopic ellipsometer according to the exemplary embodiment of the present invention may include a light source 110, an achromatic aberration collimator 120, a first polarizer 130, a first hollow shaft stepping motor 140, a second polarizer 150, a hollow shaft constant velocity rotating motor 160, a sample 200, and a sample stage 210 that are disposed on a path of incident light 100 and a second hollow shaft stepping motor 310, a third polarizer 320, an achromatic aberration optical focus system 330, an optical fiber 340, and a multichannel spectrometer 350 that are disposed on a path of reflected light 300, and the like.

In FIG. 2, the light source 110 may be a xenon lamp, a tungsten-halogen lamp, a deuterium lamp, and the like, or may be a lamp that transfers light emitted from the lamp through an optical fiber, and the like, wherein the white incident light 100 emitted from the light source 110 is changed into a parallel light by the achromatic aberration collimator 120.

Figure 4:
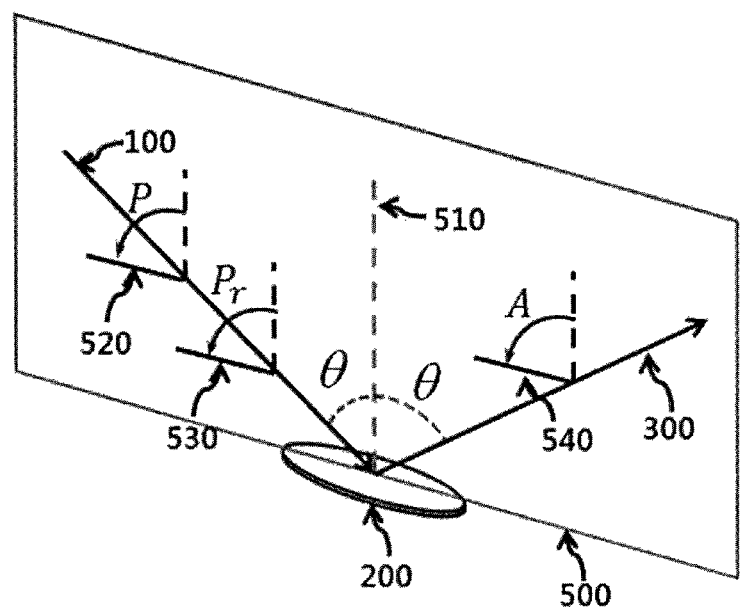
FIG. 4 is a conceptual diagram for describing an operation principle of the multichannel spectroscopic ellipsometer according to a first exemplary embodiment of the present invention.

The parallel light transmitting the achromatic aberration collimator 120 is linearly polarized by the first polarizer 130 and a transmitting-axis direction of the first polarizer stops at a position of an azimuth P with respect to the incident surface as shown in FIG. 4. The linear polarization transmitting through the first polarizer transmits the second polarizer 150 attached to the hollow shaft motor 160 rotating at constant velocity and then, is incident to a top surface of the sample 200. In this case, in the transmitting-axis direction of the second polarizer attached to the hollow shaft motor rotating at constant velocity, an azimuth $P_r$ with respect to an incident surface 500 is described with $P_r$ as shown in FIG. 4 and rotates at constant velocity over time.

When the polarization state is changed due to the reflection by the sample 200, the reflected light 300 having only polarization components in a direction in which the azimuth with respect to the incident surface is A as shown in FIG. 4 is transmitted by the third polarizer 320. The linearly polarized parallel light transmitting the third polarizer is condensed to a local area by the achromatic aberration optical focus system 330, the condensed light transmits the optical fiber 340 or directly irradiated and transferred to a slit of the multichannel spectrometer 350 and the light transferred to the multichannel spectrometer 350 is separated for each wavelength by a dispersion optical system 352 and irradiated to the multichannel photometric detector 354, the light irradiated to the multichannel photometric detector 354 is obtained as the value, that is, the exposure obtained by measuring the quantity of light for each wavelength for the predetermined integration time $T_i$ by each pixel of the multichannel photometric detector 354, and Fourier coefficients, ellipsometric angles ψ and Δ, and unpolarized reflectivity $R_u$ are operated from the measured exposure. The multichannel spectroscopic ellipsometer preferably includes an operation processor (not shown) for operation.

A theoretical equation for the ellipsometric function suitable for the sample is set and usable property information for the sample such as a thin film thickness, a refractive index, a shape dimension of a nano pattern, and the like, can be obtained by analysis of a least-squares algorithm so that the theoretical equation is optimized for the measured value.

FIG. 3 shows a multichannel spectroscopic ellipsometer according to another exemplary embodiment of the present invention. In FIG. 2, the position of the second polarizer 150 and the hollow shaft constant velocity rotating motor 160 is changed and disposed on the path of the reflected light after the sample 200 on the optical path.

In FIGS. 2 and 3, the polarizers mainly use a prism type of a linear polarizer that is made of $MgF_2$, $SiO_2$, $CaCO_3$, $YVO_4$, or a-BBO crystal, and the like.

In the exemplary embodiment of FIGS. 2 and 3, the first polarizer 130 and the third polarizer 320 may be each attached to the hollow shaft stepping motors 140 and 310 to control each azimuth through a computer and is in a stop state at the time of measurement.

In the rotating-polarizer multichannel spectroscopic ellipsometer of the related art, the light source needs to have characteristics in which the intensity of light is constant with respect to all the polarization directions. In the rotating-polarizer multichannel spectroscopic ellipsometer of the related art, as the light source, a xenon lamp, a tungsten-halogen lamp, a deuterium lamp, or a light source apparatus devised to simultaneously emit light by the deuterium lamp and the tungsten-halogen lamp are mainly used. The light source apparatuses have the residual polarization characteristics in which the intensity of light partially polarized in a direction is relatively larger than other directions and therefore, the spectroscopic ellipsometers need to correct error due to the residual polarization.

As described above, since it is difficult to implement a light source apparatus having no residual polarization in the rotating-polarizer multichannel spectroscopic ellipsometer of the related art, the rotating-element multichannel spectroscopic ellipsometer of the present invention instead uses the linearly polarized light source by additionally introducing the first polarizer 130 in a stop state between the light source 110 and the second polarizer 150 rotating at constant velocity to solve the residual polarization problem of the light source.

In the case of the rotating-analyzer multichannel spectroscopic ellipsometers of the related art, in order to accurately measure the state in which the polarization state of the light incident to the sample is changed due to the reflection or transmission due to the sample, the multichannel spectrometer capable of measuring the intensity of light incident to the multichannel spectrometer independent of the polarization direction is used. However, in the multichannel spectrometers used in the rotating-analyzer multichannel spectroscopic ellipsometers of the related art, a reflective dispersion optical systems such as a reflection mirror for collimation and a diffracting grating is used and when the linear polarization having the constant intensity of light is transferred to the multichannel spectrometer, the intensity of light may be differently measured according to the change of the polarization direction of the transferred light. Therefore, in the rotating-element multichannel spectroscopic ellipsometers of the present invention, as shown in FIG. 3, the third polarizer 320 in the stop state is additionally mounted between the second polarizer 150 rotating at constant velocity and the optical focus system 330 to transfer only the linear polarization in a specific polarization direction to the multichannel spectrometer 350, thereby solving the polarization dependency problem of the multichannel spectrometer due to the change in the polarization direction.

In the multichannel spectroscopic ellipsometer of the present invention, the optical fiber 340 is formed of a single optical fiber or a light receiving unit side is formed of a bundle of a single optical fiber and a side connected to the multichannel spectrometer may use a bundle of branched optical fiber formed of a bundle of at least two optical fibers. The dispersion optical system 352 may be configured of a slit and a diffracting grating or only the diffracting grating. The multichannel photometric detector 354 is configured of a CCD, a CMOS, or a photodiode device, wherein a plurality of pixels are arranged in a linear or two-dimensional plane structure. The multichannel spectrometer 350 has a function of maintaining a standby state before the external trigger is transferred and then, starting to measuring the quantity of light for the integration time set for each pixel of the multichannel photometric detector 354 when the external trigger is transferred and selectively includes a buffer memory for arbitrarily storing the measured data.

If it is assumed that there is no error in the rotating-element multichannel ellipsometer, the Equation (1) about the intensity of light measured by the photometric detector using the electrical signal such as voltage or current for the specific wavelength may be represented by the following Equation (4).

$$I(t) = I_{dc} + \sum_{n=1}^{N} [A_{2n}\cos(4\pi nt/T) + B_{2n}\sin(4\pi nt/T)] \quad (4)$$

In the above Equation (4), $I_{dc}$ may represent the average value of the intensity of light (referred to as a 0-order Fourier coefficient), $A_{2n}$ and $B_{2n}$ may represent the non-normalized Fourier coefficients, and T may represent the dynamic period of the optical element rotating at constant velocity. The optical element rotating at constant velocity in the rotating-element ellipsometer is selected as the linear polarizer or the compensator and therefore, waveforms of 2n-order component have characteristics having a period of T/(2n) in the waveform of the intensity of light due to the optical symmetry thereof.

In the present invention, in order to analyze the waveform of the intensity of light periodically changing over time as in the above (4), when the exposure is measured by being divided M times at a predetermined time interval for the time when the p-th rotation of the optical element rotating at constant velocity, that is, for the measuring period pT by using the integration photometric detector 354, the exposure $S_j$ measured for each pixel of the multichannel photometric detector 354 for the specific delay time $T_d$ and any integration time $T_i$ of the multichannel photometric detector 354 may be represented by the generalized Equation.

$$S_j = \int_{(j-1)pT/M+T_d}^{(j-1)pT/M+T_d+T_i} I(t)dt, \ (j=1,2,3,\ldots,M) \quad (5)$$

In the above Equation (5), the delay time $T_d$ may be changed according to the kind of the multichannel photometric detector 354 and has the specific value. When the measuring command such as the external trigger is transferred to the multichannel spectrometer 350, the photometric detector does not react with the received light for the measuring prepare time such as initializing the state of each pixel in the multichannel photometric detector 354 and therefore, the delay time is introduced into the exposure Equation of Equation (5) in consideration of this aspect. When considering the symmetry of the rotating optical elements such as the linear polarizer or the compensator in the rotating-element ellipsometer according to the exemplary embodiment of the present invention, the value of the number p of measuring periods may be freely selected as one of multiples of ½ and therefore, the maximum value of the settable integration time can be changed to pT/M. However, in the related art, a value of p is fixed to ½ or 1 and therefore, the maximum values of the set integration time each needs to be set as T/(2M) or T/M.

When Equation (4) is substituted into Equation (5), $$S_j = I_{dc}T_i + \sum_{n=1}^{N} \frac{T}{2n\pi}\sin\left(\frac{2n\pi T_i}{T}\right)\left\{\cos\left(\frac{4n\pi(j-1)p}{M}\right)\left[A_{2n}\cos\left(\frac{2n\pi(T_i+2T_d)}{T}\right)+B_{2n}\sin\left(\frac{2n\pi(T_i+2T_d)}{T}\right)\right]-\sin\left(\frac{4n\pi(j-1)p}{M}\right)\left[A_{2n}\sin\left(\frac{2n\pi(T_i+2T_d)}{T}\right)-B_{2n}\cos\left(\frac{2n\pi(T_i+2T_d)}{T}\right)\right]\right\} \quad (6)$$

is obtained. The measuring Equation of exposure of Equation (6) uses the discrete Fourier transform using orthogonality of a trigonometric function such as the following Equations (7), (8), and (9)

$$d_0 = \frac{1}{M}\sum_{j=1}^{M} S_j \quad (7)$$

$$a_{2n} = \frac{2}{M}\sum_{j=1}^{M} S_j\cos\left(\frac{4n\pi(j-1)p}{M}\right) \quad (8)$$

$$b_{2n} = \frac{2}{M}\sum_{j=1}^{M} S_j\sin\left(\frac{4n\pi(j-1)p}{M}\right) \quad (9)$$

$$I_{dc} = d_0/T_i \quad (10)$$

$$A_{2n} = \frac{\xi_{2n}}{T_i\sin(\xi_{2n})}\left\{a_{2n}\cos\left[\xi_{2n}\left(1+\frac{2T_d}{T_i}\right)\right]-b_{2n}\sin\left[\xi_{2n}\left(1+\frac{2T_d}{T_i}\right)\right]\right\} \quad (11)$$

$$B_{2n} = \frac{\xi_{2n}}{T_i\sin(\xi_{2n})}\left\{a_{2n}\sin\left[\xi_{2n}\left(1+\frac{2T_d}{T_i}\right)\right]+b_{2n}\cos\left[\xi_{2n}\left(1+\frac{2T_d}{T_i}\right)\right]\right\} \quad (12)$$

In the above equation, the $I_{dc}$ represents the average value of the intensity of light of Equation (4) and the non-normalized Fourier coefficients $A_{2n}$ and $B_{en}$ for any order $2n$ are obtained. Here, $\xi_n = n\pi T_i/T$. $d_0$, $a_{2n}$, and $b_{2n}$ of Equations (7) to (9) are obtained from the exposure $S_j$ measured for any integration time $T_i$ at a predetermined time interval $pT/M$ for the arbitrarily set measuring frequency M for exposure and when these values are substituted into Equations 10 to 12, experimental values for $I_{dc}$, $A_{2n}$, and $B_{2n}$ can be obtained.

Generally, even though the light from the light source is blocked, the multichannel photometric detectors may have a background signal due to thermal noise and the unintended light by environmental lighting, and the like and therefore, the error occurs when these aspects are not considered. Therefore, as shown in FIGS. 2 and 3, a remote light source blocking apparatus 410 is installed after the light source 110 on the optical path to block the light emitted from the light source 110 before measurement, thereby measuring the background signal. In this case, when the measured value of the background signal is subtracted from the measured value of the exposure, the error due to the background signal is removed.

In the exemplary embodiment of the present invention, in order to more easily measure the Fourier coefficients for the waveform of the intensity of light, the digital signal modulating apparatus 430 as shown in FIGS. 2 and 3 is introduced so as to arbitrarily change the number of measuring periods and the measuring frequency of exposure and the detailed flow chart thereof is shown in FIG. 5. In this case, the digital signal modulating apparatus 430 may be preferably configured of a field-programmable gate array (FPGA) integrated circuit and a computer controlling it but may appropriately use other processors.

As shown in FIGS. 2 and 3, the second polarizer 150 is attached to the hollow shaft motor 160 rotating at constant velocity at the time period T, such that the second polarizer 150 and the hollow shaft motor 160 rotate together. The hollow shaft motor 160 may change control input voltage to control a rotating speed. An optical encoder attached to the hollow shaft motor 160 generates one reference pulse for each rotation of the time period T and clock pulses that are set to be a natural number of several hundreds or more. Here, the reference pulse is used to find the reference point with respect to the incident surface of the azimuth of the second polarizer 150 of FIG. 4.

As shown in FIG. 5, in the rotating-element multichannel spectroscopic ellipsometer according to the exemplary embodiment of the present invention, the value of the measuring frequency M of exposure per unit measurement is selected as one of divisors for a total number of clock pulses generated per unit measurement by the optical encoder and the pulse modulating program of the digital signal modulating apparatus 430 can be changed by computer software. Therefore, the integration time $T_i$ of the multichannel photometric detector 354 may be set to be equal to or smaller than the value of pT/M and therefore, the maximum value of the integration time may be controlled by changing the M value and the p value. When the clock pulses generated from the encoder are transferred to the digital signal modulating apparatus 430 along a signal transmission line 420, the spectrometer operating triggers are generated by a total number M and an equidistance pT/M by the digital signal modulating apparatus 430. When the spectrometer operating triggers generated as described above are transferred to the multichannel spectrometer 350 by another signal transmission line 440, the exposure is measured for the integration time set at each pixel whenever the multichannel photometric detector 354 receives the spectrometer operating triggers. $d_0$, $a_{2n}$, and $b_{2n}$ of Equations (7) to (9) are obtained from the exposure measured for the arbitrarily set measuring frequency M of exposure and when these values are substituted into Equations 10 to 12, the experimental values for $I_{dc}$, $A_{2n}$, and $B_{2n}$ may be obtained. The ellipsometer includes an operator (not shown) performing the foregoing operation to acquire the plurality values of exposure for the waveform of the intensity of light at a predetermined interval for any multiple of the period T from the multichannel photometric detector 354 and performs the discrete Fourier transform on the plurality of values of exposure to determine the plurality of Fourier coefficients and the average value component of the waveform of the intensity of light.

Finally, the ellipsometric functions are obtained from the measured Fourier coefficients.

In the rotating-element multichannel ellipsometers of the present invention as shown in FIGS. 2 and 3, the relationship Equation between the ellipsometric angles $\psi$ and $\Delta$ are obtained from the Fourier coefficients related to the waveform of the intensity of light as described above.

FIG. 4 is a diagram showing an azimuth of the polarizers of a case of the rotating-element multichannel spectroscopic ellipsometer according to an exemplary embodiment of the present invention as shown in FIG. 2. Here, the incident surface 500 is vertical to the surface of the sample 200 and is defined as a plane in which the path of the incident light 100 and the path of the reflected light 300 exists. When the incident light 100 is irradiated to a shaft 510 vertical to the sample 200 at an incident angle θ, the incident light 100 is reflected at the same angle θ by the sample 200 and thus, becomes the reflected light 300. The azimuths of a transmitting axis 520 of the first polarizer, a transmitting axis 530 of the second polarizer, and a transmitting axis 540 of the third polarizer for the incident surface 500 are each represented by P, $P_r$, and A. The hollow shaft stepping motor is used in order to control the azimuths of the first polarizer and the third polarizer and the hollow shaft constant velocity rotating motor manufactured by a DC motor, an AC motor, or a stepping motor is used in order to rotate the second polarizer at constant velocity.

When the measuring system is applied to the sample having isotropic optical characteristics as shown in FIG. 4, the incident light is described by a Stokes vector and the polarizers and the sample are each described by a Mueller matrix to calculate the intensity of light transmitting the third polarizer for any one waveform. In this case, the follow theoretical Equation is given.

$$I(P_r) = I_{dc} + A_2\cos(2P_r) + B_2\sin(2P_r) + A_4\cos(4P_r) + B_4\sin(4P_r) \quad (13)$$

$$I_{dc} = \frac{I_{00}}{2} \{2 + \cos(2A)\cos(2P) - N[2\cos(2A) + \cos(2P)] + C\sin(2A)\sin(2P)\} \quad (14)$$

$$A_2 = I_{00}\{\cos(2P) + \cos(2A) - N[1 + \cos(2A)\cos(2P)]\} \quad (15)$$

$$B_2 = I_{00}[\sin(2P) - N\cos(2A)\sin(2P) + C\sin(2A)] \quad (16)$$

$$A_4 = \frac{I_{00}}{2}[\cos(2A)\cos(2P) - N\cos(2P) - C\sin(2A)\sin(2P)] \quad (17)$$

$$B_4 = \frac{I_{00}}{2}[\cos(2A)\sin(2P) - N\sin(2P) + C\sin(2A)\cos(2P)] \quad (18)$$

In the above Equations, N and C are functions defined by the ellipsometric angles ψ and Δ like N=cos(2ψ) and C=sin(2ψ) cos(Δ) and the common component $I_{00}$ is defined by a product of $T_s$ that is related to transmittance for the optical system of the ellipsometer by non-polarization reflectivity $R_u$ due to the sample. Even for the samples having the anisotropic optical characteristics, an identical equation for the Fourier coefficients may be induced using a method similar to the foregoing method.

In the single channel spectroscopic ellipsometers configured of three polarizer of the related art, an equation obtaining the ellipsometric functions ψ, Δ, and $R_u$ using all the simultaneous equations for four Fourier coefficients are used is used and therefore, the measuring precision may be relatively degraded. Therefore, when the simultaneous equation is solved by optionally selecting the Fourier coefficients with relatively excellent measurement conditions to use the results obtaining the solutions for N and C, the characteristic of the measuring precision may be better than the measured result of the related art.

The simultaneous equations (14) to (18) are described by three unknown parameters $I_{00}$, N, and C and therefore, at least three simultaneous equations are required to obtain the unknown parameters. When the simultaneous equations (14) to (16) are selected, $$I_{00} = \frac{2[2I_{dc} - A_2\cos(2P) - B_2\sin(2P)] + \cos(2A)\{4I_{dc}\cos(2P) - A_2[3 + \cos(4P)] - B_2\sin(4P)\}}{2\sin^2(2A)} \quad (19)$$

$$N = \frac{4I_{dc}\cos(2P) - A_2[3 + \cos(4P)] + 2\cos(2A)}{4I_{dc} - 2A_2\cos(2P) - 2B_2\sin(2P) + \cos(2A)\{4I_{dc}\cos(2P) - A_2[3 + \cos(4P)] - B_2\sin(4P)\}} \quad (20)$$

$$C = \frac{\sin(2A)\{A_2\sin(4P) + B_2[3 - \cos(4P)] - 4I_{dc}\sin(2P)\}}{4I_{dc} - 2A_2\cos(2P) - 2B_2\sin(2P) + \cos(2A)\{4I_{dc}\cos(2P) - A_2[3 + \cos(4P)] - B_2\sin(4P)\}} \quad (21)$$

The solutions for the unknown parameters are obtained by Equations (19) to (21) Therefore, when the experimental values for $I_{dc}$, $A_2$, and $B_2$ are obtained using the Equations (10) to (12), the obtained experimental values are substituted into the Equations (19) to (21) to obtain the experimental values for the unknown parameters. When the experimental value of the $I_{00}$ measured for one sample is divided by the experimental value of $T_s$ measured by removing the sample and forming the optical system in a straight state, the experimental value $R_u$ of the non-polarization reflectivity due to the sample can be obtained. Therefore, the experimental values of $R_u$, N, and C that are parameters related to the properties of the sample are measured and the theoretical Equation therefor can be established and therefore, the values of the theoretical Equation established using the least-squares algorithm coincide with the experimental values, thereby obtaining the properties of the sample. The method may be applied to several combinations of selecting at least three of five simultaneous Equations (14) to (18) to obtain the experimental values of $R_u$, N, and C. In this case, when the number of simultaneous Equations is 4 or 5, the number of simultaneous Equations is reduced by the number of unknown parameters by operations such as addition, subtraction, or division of a part of the simultaneous Equations, and the like, thereby obtaining the solution for the unknown parameters. For example, when the simultaneous Equations (15) to (18) are selected, the following Equations (22) to (24) are given.

$$I_{00} = \frac{2[U_2\cos(2P) + V_2\sin(2P) - 2U_4] + \cos(2A)[U_2 - 4U_4\cos(2P) - V_2\cos(4P) - U_2\sin(4P)]}{2\sin^2(2A)[\cos(4P) + \sin(4P)]} \quad (22)$$

$$N = \frac{U_2 - 4U_4\cos(2P) - V_2\cos(4P) + 2\cos(2A)}{2U_2\cos(2P) - 4U_4 + 2V_2\sin(2P) + \cos(2A)} \frac{[U_2\cos(2P) - 2U_4 + V_2\sin(2P)] - U_2\sin(4P)}{[U_2 - 4U_4\cos(2P) - V_2\cos(4P)] - U_2\sin(4P)} \quad (23)$$

$$C = \frac{\sin(2A)[U_2\cos(4P) + 4U_4\sin(2P) - V_2\sin(4P) - V_2]}{2U_2\cos(2P) - 4U_4 + 2V_2\sin(2P) + \cos(2A)} \frac{}{[U_2 - 4U_4\cos(2P) - V_2\cos(4P)] - U_2\sin(4P)} \quad (24)$$

Here, $U_2=A_2+B_2$, $U_4=A_4+B_4$, and $V_2=A_2-B_2$.

In Equations (14) to (18), the Fourier coefficients such as $I_{dc}/I_{00}$, $A_2/I_{00}$, $B_2/I_{00}$, $A_4/I_{00}$, and $B_4/I_{00}$ or $I_{dc}/T_{oo}$, $A_2/I_{dc}$, $B_2/I_{dc}$, $A_4/I_{dc}$, and $B_4/I_{dc}$ are the properties of the sample and the functions of the azimuths of the first polarizer and the third polarizer and therefore, the properties of the sample may be immediately obtained from the experimental values thereof.

The normalized Fourier coefficients from the non-normalized Fourier coefficients of Equations (15) to (18) are obtained by the following Equations (25) to (28).

$$\alpha_2 = A_2/I_{dc} \quad (25)$$

$$\beta_2 = B_2/I_{dc} \quad (26)$$

$$\alpha_4 = A_4/I_{dc} \quad (27)$$

$$\beta_4 = B_4/I_{dc} \quad (28)$$

When only the $\alpha_2$ and $\beta_2$ among the normalized Fourier coefficients are selected, they are obtained by the following Equations (29) and (30).

$$N = \frac{[2-\alpha_2\cos(2P)-\beta_2\sin(2P)]-\beta_2\sin(4P)}{4-2\alpha_2\cos(2P)-2\beta_2\sin(2P)+\cos(2A)} \quad \frac{4\cos(2P)-\alpha_2[3+\cos(4P)]+2\cos(2A)}{\{4\cos(2P)-\alpha_2[3+\cos(4P)]-\beta_2\sin(4P)\}} \quad (29)$$

$$C = \frac{\sin(2A)\{\alpha_2\sin(4P)+\beta_2[3-\cos(4P)]-4\sin(2P)\}}{4-2\alpha_2\cos(2P)-2\beta_2\sin(2P)+\cos(2A)} \quad \frac{}{\{4\cos(2P)-\alpha_2[3+\cos(4P)]-\beta_2\sin(4P)\}} \quad (30)$$

When the simultaneous equations (15) to (18) are selected, in the equations (23) and (24), the values of N and C can each be obtained by substituting $U_2=\alpha_2+\beta_2$, $U_4=\alpha_4+\beta_4$, and $V_2=\alpha_2-\beta_2$. Therefore, when a part of the Fourier coefficients having the relatively excellent measurement condition is selected, the values of N and C may be obtained therefrom. The ellipsometric angles are calculated by the following Equations (31) and (32).

$$\Psi = \frac{1}{2}\cos^{-1}(N) \quad (31)$$

$$\Delta = \cos^{-1}\left(\frac{C}{\sqrt{1-N^2}}\right) \quad (32)$$

The relationship Equation between the Fourier coefficients and the ellipsometric angles in the case of the rotating-element multichannel spectroscopic ellipsometers of the present invention as shown in FIG. 3 is obtained by replacing the azimuth P with A and the azimuth A with P in the above Equations (14) to (30) of FIG. 2.

In the case of the semiconductor industry, a size of the test region to be measured in the sample is very small at several tens of μm and therefore, as in FIGS. 2 and 3, the achromatic aberration optical focus system 450 that focuses the incident light 100 on a test region in the sample 200 is installed in a path in front of the sample stage 210 and the achromatic aberration collimator 460 that again changes the light reflected or transmitted by the sample 200 into the parallel light may be selectively provided. Here, the achromatic aberration optical focus systems 330 and 450 and the achromatic aberration collimators 120 and 460 may be configured of an optical system including at least one mirror for correcting chromatic aberration for the broadband wavelength or at least one lens made of heterogeneous materials, or at least one mirror and at least one lens and may adopt the lenses or the mirrors coated with a single thin film or a multi-layer thin film in order to improve transmission efficiency or reflection efficiency.

The sample stage 210 may be configured a 6 free degree system that can implement a parallel movement of 3 free degrees vertically and horizontally and includes a gradient control having 2 free degrees and a rotation function in order to change the alignment and the measured position of the sample 200 and may include a vacuum chuck in order to maintain the sample on the sample stage in a stop state at the time of measurement.

For the alignment of the sample for measurement, a sample alignment system including a laser emitting light for sample alignment, an optical system inputting light emitted from the laser to the sample in a specific direction, and a photometric detector receiving light reflected due to the sample with respect to the incident light and determining the position of the received light may be provided.

In order to reduce the error due to the change in the measuring environment, the multichannel spectroscopic ellipsometer of the present invention may include an apparatus that makes the optical path into the atmospheric state of nitrogen gas or argon gas, and the like, to measure the broadband wavelength and in order to reduce an effect due to the vibration of the system and the measuring environment, the multichannel spectroscopic ellipsometer may be mounted on a vibration isolation system and may include a constant temperature system in order to reduce the measuring error due to the change in temperature for the light source, the optical elements, the sample, and the multichannel spectrometer.

In particular, in the case of the semiconductor industries, it is important for the multichannel spectroscopic ellipsometer to measure the plurality of wafer samples in a rapid time. To this end, the multichannel spectroscopic ellipsometer may include a sample container capable of storing samples and a sample delivery apparatus that sequentially takes out the samples from the sample container and moves the samples to the sample stage and when the measurement for the designated points completes, again delivers the sample disposed on the sample stage on the sample container so as to measure the properties of the sample.

The multichannel spectroscopic ellipsometer according to the exemplary embodiment of the present invention may analyze various properties such as interfacial characteristic, a thin film thickness, a complex refractive index, a nano shape, anisotropic characteristic, surface roughness, a composition ratio, crystallinity, and the like, of the sample from the measured Fourier coefficients or the measured ellipsometric functions.

The multichannel spectroscopic ellipsometer can be used for measuring equipment for a semiconductor device process, measuring equipment for a flat display process, measuring equipment for a solar cell, measuring equipment for a thin film optics, a bio sensor, or a gas sensor, and the like.

In particular, in the multichannel spectroscopic ellipsometer according to the exemplary embodiment of the present invention, a method for analyzing properties in the case in which an analysis method such as a method for measuring a nano pattern shape is very complex first obtains the measuring data of the Fourier coefficients or the ellipsometric functions for the sample, establishes the optical theory for the sample, obtains the data of the Fourier coefficients or the ellipsometric functions calculated using the values of the plurality of unknown parameters defined in the region set for the established theoretical equation, forms the continuous function for the unknown parameters for the calculated data, and optimizes the continuous function by applying the least-squares algorithm to the measuring data, thereby obtaining the properties of the sample. In this case, the multichannel spectroscopic ellipsometer according to the exemplary embodiment of the present invention may include a large-capacity high-speed operation system configured of a high-performance parallel computer, a rigorous coupled-wave analysis (RCWA) algorithm based analysis software, and a large-capacity data storage so as to rapidly find the properties of the sample from the measuring data of the Fourier coefficients or the ellipsometric functions measured for the sample.

The multichannel spectroscopic ellipsometer according to the exemplary embodiment of the present invention may include an apparatus that rotates in a single direction or plurality of measuring directions to the sample, or in the single or plurality of azimuths P and A, or in the single or plurality of incident angles θ to measure the sample.

The multichannel spectroscopic ellipsometer according to the exemplary embodiment of the present invention can measure the Mueller matrix components of the sample to analyze the properties of the sample.

In the multichannel spectroscopic ellipsometer according to the exemplary embodiment of the present invention, in order to obtain the measured values for the entire region of 0° to 360° for Δ representing the phase difference among the ellipsometric functions, at least one compensator disposed before or after the sample stage 210 on the progress path of light of FIGS. 2 and 3 may be provided.

By the configuration as described above, the rotating-element ellipsometer according to the exemplary embodiment of the present invention can more easily measure the Fourier coefficients for a waveform of the intensity of light by controlling the integration time and the measuring frequency of exposure according to the intensity of light by solving the problems of the limitation of the integration time of the photometric detector in the rotating-element ellipsometer of the related art.

The rotating-element ellipsometer according to the exemplary embodiment of the present invention can improve the measuring precision by rapidly and easily changing the integration time and the measuring frequency of exposure with the computer software.

According to the exemplary embodiment of the present invention, the Fourier coefficients for the waveform of the intensity of light are more easily acquired by improving the measuring precision without adding the optical system and the Fourier coefficients for the waveform of the intensity of light are more precisely acquired by the simple calculation, thereby accurately measuring the properties of the sample.

By the foregoing means, the rotating-element multichannel spectroscopic ellipsometer according to the exemplary embodiment of the present invention is configured of three linear polarizers having the an achromatic aberration characteristics to optimally perform the spectroscopic measurement of the broadband wavelength region and solves the residual polarization problem of the light source and the polarization dependency problem of the multichannel photometric detector to improve the measuring accuracy.

The multichannel spectroscopic ellipsometer according to the exemplary embodiment of the present invention includes the digital signal modulating apparatus to easily change the measuring period, the measuring frequency of exposure, and the integration time so as to implement better measuring conditions, thereby more rapidly and accurately measuring the properties of the sample in real time.

The present invention is not limited to the aforementioned exemplary embodiment and an application range is various and it is apparent that various modifications can be made to those skilled in the art without departing from the spirit of the present invention described in the appended claims.

What is claimed is:

1. An ellipsometer, comprising:
a light source emitting white light to a sample;
an achromatic aberration collimator disposed between the light source and the sample stage on a progress path of light and forming the white light emitted from the light source into parallel light;
a first polarizer disposed between the achromatic aberration collimator and the sample stage on the progress path of light and receiving the parallel light and polarizing the parallel light;
a sample stage supporting the sample;
a second polarizer disposed at the front or rear of the sample and rotating at constant velocity for polarizing the incident light;
a third polarizer disposed at the rear of the sample and polarizing the incident light;
an achromatic aberration optical focus system receiving the light transmitting the third polarizer and intensively irradiating the incident light to a local region of a multichannel spectrometer; and
a multichannel spectrometer receiving the light transferred by the achromatic aberration optical focus system, separating the incident light for each wavelength using the dispersion optical system, irradiating the light separated for each wavelength to the multichannel photometric detector, and measuring the exposure of light irradiated to the multichannel photometric detector for each pixel of the multichannel photometric detector,
whereby properties of the sample are measured.

2. The ellipsometer of claim 1, further comprising:
a digital signal modulating apparatus for controlling the number of measuring periods and the measuring frequency of exposure,
wherein the digital signal modulating apparatus controls the integration time of the photometric detector according to measuring conditions of the intensity of light irradiated to the multichannel photometric detector.

3. The ellipsometer of claim 1, wherein a plurality of Fourier coefficients $I_{dc}$, $A_2$, $B_2$, $A_4$, and $B_4$ are calculated by performing discrete Fourier transform on the exposure measured for the integration time arbitrarily set by the multichannel photometric detector at a predetermined time interval for time (pT: p=½, 1, 3/2, 2, . . . ) of a multiple of ½ of the optical element turn period T.

4. The ellipsometer of claim 3, wherein ψ, Δ, and $R_u$ or N, C, and $R_u$ are calculated from at least three of the plurality of Fourier coefficients.

5. The ellipsometer of claim 4, wherein ellipsometric functions are obtained by limitedly selecting the Fourier coefficients among the Fourier coefficients $I_{dc}$, $A_2$, $B_2$, $A_4$, and $B_4$.

6. The ellipsometer of claim 1, wherein properties for the sample of interfacial characteristic, a thin film thickness, a complex refractive index, a nano shape, anisotropic characteristic, surface roughness, a composition ratio, crystallinity are analyzed from the measured Fourier coefficients $I_{dc}/I_{00}$, $A_2/I_{00}$, $B_2/I_{00}$, $A_4/I_{00}$, and $B_4/I_{00}$ or $I_{dc}/I_{00}$, $A_2/I_{dc}$, $B_2/I_{dc}$, $A_4/I_{dc}$, and $B_4/I_{dc}$ or the measured ellipsometric functions ψ, Δ, and $R_u$ or N, C, and Ru.

7. The ellipsometer of claim 1, wherein the measuring data of the measured Fourier coefficients $I_{dc}$, $A_2$, $B_2$, $A_4$, and $B_4$ or the measured ellipsometric functions ψ, Δ, and $R_u$ or N, C, and $R_u$ are obtained, the optical theoretical Equation for the sample is established, the data of the Fourier coefficients or the ellipsometric functions calculated using the plurality of unknown parameters for the region set for the established theoretical Equation are obtained, the continuous function for the unknown parameters is obtained from the data obtained from the calculation, and the properties of the sample are obtained by optimizing the continuous function by applying the least-squares algorithm to the measuring data.

8. The ellipsometer of claim 1, wherein the multichannel photometric detector is configured of CCD, CMOS, or photodiode devices and the plurality of pixels are arranged in a linear or two-dimensional plane structure.

9. The ellipsometer of claim 1, further comprising: a remote light source blocking apparatus disposed after the light source on the progress path of light and blocking the light irradiated to the sample from the light source by a remote control.

10. The ellipsometer of claim 1, further comprising:
a first hollow shaft stepping motor attached to the first polarizer to control an azimuth of the first polarizer;
a second hollow shaft stepping motor attached to the third polarizer to control an azimuth of the third polarizer;
a hollow shaft constant velocity rotating motor attached to the second polarizer to rotate the second polarizer at constant velocity; and
an optical encoder attached to the hollow shaft constant velocity rotating motor to rotate like the hollow shaft constant velocity rotating motor and generating one reference pulse and a plurality of clock pulses for each rotation.

11. The ellipsometer of claim 10, wherein the clock pulses generated from the encoder are transferred to the digital signal modulating apparatus, the digital signal modulating apparatus generates the specific number of spectrometer operating triggers at equidistance by the pulses, and the generated spectrometer operating triggers are transferred to the multichannel spectrometer to measure the exposure for the integration time set at each pixel whenever the multichannel photometric detector receives the spectrometer operating trigger.

12. The ellipsometer of claim 11, wherein the digital signal modulating apparatus changes the measuring period or the measuring frequency of exposure according to the intensity of light irradiated to the multichannel photometric detector.

13. The ellipsometer of claim 1, further comprising:
an optical fiber disposed between the achromatic aberration optical focus system and the multichannel spectrometer,
wherein the optical fiber is a single optical fiber or a light receiving unit side is a bundle of a single optical fiber and a side connected to the multichannel spectrometer is a bundle of a branched optical fiber formed of a bundle of at least two optical fibers.

* * * * *